(12) United States Patent
Carter et al.

(10) Patent No.: US 8,696,630 B2
(45) Date of Patent: Apr. 15, 2014

(54) DETACHABLE DRUG DELIVERY DEVICE

(75) Inventors: Brett J. Carter, Monroe, WA (US);
Brett Cross, Seattle, WA (US); John McKenzie, San Carlos, CA (US)

(73) Assignee: Calibra Medical, Inc., Redwood City, CA (US)

( * ) Notice: Subject to any disclaimer, the term of this patent is extended or adjusted under 35 U.S.C. 154(b) by 35 days.

(21) Appl. No.: 13/358,764

(22) Filed: Jan. 26, 2012

(65) Prior Publication Data

US 2012/0197199 A1  Aug. 2, 2012

Related U.S. Application Data

(60) Provisional application No. 61/437,424, filed on Jan. 28, 2011.

(51) Int. Cl.
*A61M 1/00* (2006.01)

(52) U.S. Cl.
USPC ........... 604/151; 604/131; 604/132; 604/133; 604/153

(58) Field of Classification Search
USPC .................................. 604/131–133, 151–153
See application file for complete search history.

(56) References Cited

U.S. PATENT DOCUMENTS

| 6,500,156 | B1* | 12/2002 | Stansbury | 604/185 |
| 7,988,673 | B2* | 8/2011 | Wright et al. | 604/174 |
| 2009/0326453 | A1 | 12/2009 | Adams et al. | |
| 2009/0326454 | A1 | 12/2009 | Cross et al. | |
| 2009/0326456 | A1* | 12/2009 | Cross et al. | 604/151 |
| 2009/0326472 | A1 | 12/2009 | Carter et al. | |
| 2010/0286602 | A1 | 11/2010 | Carter et al. | |

OTHER PUBLICATIONS

PCT Notification Concerning Transmittal of Copy of International Preliminary Report on Patentability, International Application No. PCT/US2012/023136, date of mailing Aug. 8, 2013.

\* cited by examiner

*Primary Examiner* — Laura Bouchelle
(74) *Attorney, Agent, or Firm* — Wayne C. Jaeschke, Jr.

(57) ABSTRACT

A reservoir for use in a wearable infusion device includes a substantially rigid base having a perimeter, a substantially rigid top having a perimeter, and a flexible rolling diaphragm between the base and the top. The diaphragm has an outer perimeter sealed along the perimeter of the base and an inner perimeter sealed along the perimeter of the top. The diaphragm is arranged to dispose the top and the base immediately adjacent each other when the reservoir is empty and to dispose the top and the base in spaced apart relation when the reservoir is full.

16 Claims, 4 Drawing Sheets

DETACHABLE DRUG DELIVERY DEVICE

PRIORITY CLAIM

The present application claims the benefit of U.S. Provisional Patent Application Ser. No. 61/437,424, filed Jan. 28, 2011, which application is incorporated herein by reference in its entirety.

BACKGROUND OF THE INVENTION

The present invention relates to wearable infusion devices and more particularly to such devices that enable liquid medicaments to be conveniently and safely self-administered by a patient. One liquid medicament that is often self-administered by a patient is insulin, and for ease of description, the administration of insulin is generally used herein for exemplary purposes although the invention should not be limited by that exemplary use.

Administration of insulin has traditionally been accomplished using a syringe. Recently, needle carrying pen-like devices have also been employed for this purpose. Both forms of insulin administration require the patients to stick themselves each time they inject insulin, often many times a day. Additionally, a new clean needle must be mounted on the device each time they are used, and disposed of after each use, creating the additional problem of having the "sharps" with them whenever the patient needs to administer insulin, and to safely dispose of them after each use. Thus, these traditional forms of insulin administration have been a rather pervasive intrusion in the lives and routines of the patients who have had to adopt and employ them.

More recently, insulin pumps attached by tubing to an infusion set mounted on the patient's skin have been developed as an alternative form of insulin administration. Such pumps may be controlled by a programmable remote electronic system employing short range radio communication between a control device and electronics that control the pump. While such devices may involve fewer needle sticks, they are expensive to manufacture. They are also complex to operate and cumbersome and awkward to wear. Further, the cost of such devices can be many times the daily expense of using a traditional injection means such as a syringe or an insulin pen.

Devices of the type mentioned above also require a significant amount of training to control and thus use the devices. Great care in programming the devices is required because the pumps generally carry sufficient insulin to last a few days. Improper programming or general operation of the pumps can result in delivery of an excessive amount of insulin which can be very dangerous and even fatal.

Many patients are also reluctant to wear a pump device because they can be socially awkward. The devices are generally quite noticeable and can be as large as a pager. Adding to their awkwardness is their attachment to the outside of the patients clothes and the need for a catheter like tubing set running from the device to an infusion set located on the patient's body. Besides being obvious and perhaps embarrassing, wearing such a device can also be a serious impediment to many activities such as swimming, bathing, athletic activities, and many activities such as sun bathing where portions of the patient's body are necessarily uncovered.

In view of the above, a more cost effective and simple device has been proposed whereby an injection system is discreetly attached directly to the skin of the patient. One example of such a device is described in detail in U.S. application Ser. No. 12/147,283 filed Jun. 26, 2008 and titled DISPOSABLE INFUSION DEVICE WITH REDUNDANT VALVED SAFETY, which application is owned by the assignee of this application and incorporated herein by reference in its entirety. Such a device may be attached to the patient under the patient's clothing to deliver insulin into the patient by the manual pumping of small doses of insulin out the distal end of a temporarily indwelling cannula that is made a part of the pump device. The device may be made quite small and, when worn under the clothes, entirely unnoticeable in most social situations. It may still carry sufficient insulin to last a patient several days. It can be colored to blend naturally with the patient's skin color so as not to be noticeable when the patient's skin is exposed. As a result, insulin for several days may be carried by the patient discreetly, and conveniently applied in small dosages after only a single needle stick. For another description of devices of this type, reference may also be had to co-pending application Ser. No. 11/906,130, filed on Sep. 28, 2007 for DISPOSABLE INFUSION DEVICE WITH DUAL VALVE SYSTEM, which application is owned by the assignee of this application and hereby incorporated herein by reference in its entirety.

Although relatively discrete, the patient may have a reason to remove the system entirely. Likewise, if the drug delivery system is accidentally dislodged from the patient, it would be advantageous to be able to salvage the medicament and pump, and to replace only the minimum amount of the system. Where the pump, insulin supply and cannula are integral and non-separable units, removing just the pump or just the insulin, or adding a different liquid medicament is not generally feasible. Sometimes it would be advantageous to be able to remove the pump unit, the insulin reservoir, or the entire device, and to reassemble and use parts of the drug delivery system. Additionally, since the portion of system that contains the cannula needs to be removed and reinstalled every three days pursuant to current medical and regulatory practice, it would be advantageous to be able to remove the other portions of the drug delivery system from the portion with the cannula, and reattach them to a new cannula containing portion, thus avoiding replacing them with every use.

Further, it would be advantageous if the device was configured to utilize commercially available reservoirs or cartridges. It would be further advantageous if the reservoirs could be prefilled, releasing the patient from the task of filling the reservoir before the device is deployed on the patient's skin.

Unfortunately, shelf life becomes a problem with prefilled reservoirs. Most drug degradation is due to loss of moisture vapor. In order to assure adequate shelf life of a reservoir filled with insulin, for example, the reservoir materials and construction must minimize loss of moisture vapor. The present invention addresses these and other issues.

SUMMARY OF THE INVENTION

In some embodiments described herein, a reservoir for use in a wearable infusion device includes a substantially rigid base, the base having a perimeter, a substantially rigid top, the top having a perimeter, and a flexible rolling diaphragm between the base and the top. The diaphragm has an outer perimeter sealed along the perimeter of the base and an inner perimeter sealed along the perimeter of the top. The diaphragm is arranged to dispose the top and the base immediately adjacent each other when the reservoir is empty and to dispose the top and the base in spaced apart relation when the reservoir is full.

The diaphragm may have an S-shaped cross-section, an accordion-like cross-section, or a smooth cross-section. The inner perimeter of the diaphragm may be sealed along the perimeter of the top by one of thermal welding, thermal compression, laser welding, ultrasonic welding, adhesive bonding, mechanical clamping, mechanical crimping, or any combination of the above.

The reservoir may further include a clamping ring, wherein the outer perimeter of the diaphragm is in sealed confinement between the clamping ring and the perimeter of the base. The reservoir top may include a first substantially planar member and a second substantially planar member in surface contact with the first substantially planar member. The diaphragm inner perimeter may be in sealed confinement between the first and second substantially planar members.

The reservoir base may include a first member and a second member, the reservoir may further include a clamping ring, and the outer perimeter of the diaphragm may be in sealed confinement between the clamping ring and the first member of the base.

In embodiments described herein, a wearable infusion device includes a base arranged to be adhered to the skin of a patient, a cannula assembly carried on the base, a pumping unit arranged to be received on the base in fluid communication with the cannula assembly, and a reservoir arranged to be received by the pumping unit. The reservoir includes a substantially rigid base, the base having a perimeter, a substantially rigid top, the top having a perimeter, and a flexible rolling diaphragm between the reservoir base and the top. The diaphragm has an outer perimeter sealed along the perimeter of the reservoir base and an inner perimeter sealed along the perimeter of the top. The diaphragm is arranged to dispose the top and the reservoir base immediately adjacent each other when the reservoir is empty and to dispose the top and the reservoir base in spaced apart relation when the reservoir is full.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION OF THE DRAWINGS

Figure 1:
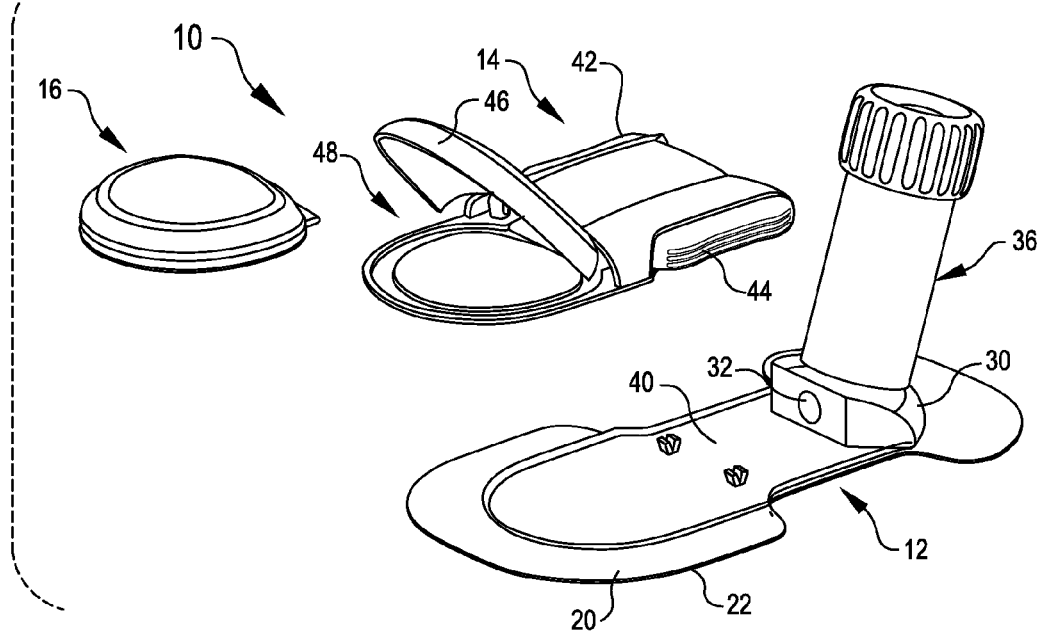
FIG. 1 is an exploded perspective view of an infusion device embodying the present invention.
Figure 2:
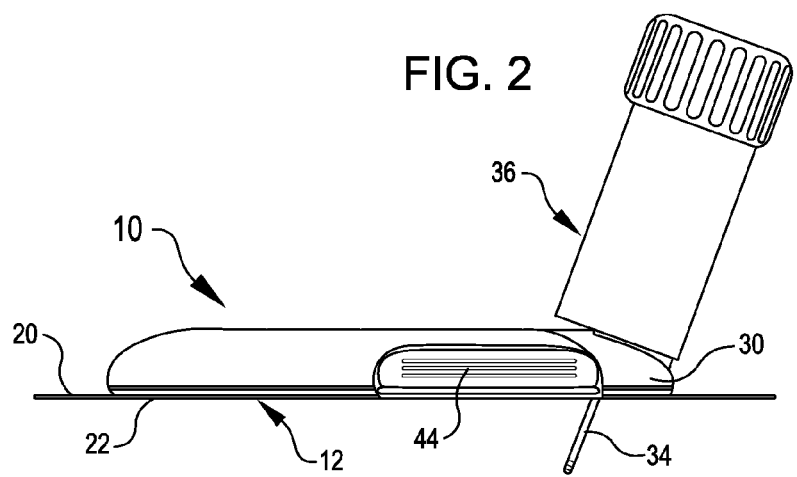
FIG. 2 is a side view of the device of FIG. 1.

FIG. 1 is an exploded perspective view of an infusion device 10 embodying the present invention and FIG. 2 is a side view of the device 10. The device 10 generally includes a base 12, a pump unit 14, and a reservoir 16.

The base 12 includes a pad 20 having an adhesive coating 22. The adhesive coating permits the device 10 to be adhered to the skin of a patient. The adhesive coating may be initially covered by a protective sheet that is striped from the coating 22 before the device is adhered to the patient's skin.

The base further includes a cannula receiver 30. Mounted on the cannula receiver is a cannula driver 36. The cannula driver 36 originally contains a cannula 34 that it drives into the cannula receiver 30 and to a deployed position with its distal end beneath the skin of the patient as shown in FIG. 2. Once the driver 36 has deployed the cannula 34, it may be removed from the cannula receiver 30 of the base 12.

The base 12 further includes a bed 40. The bed is arranged to receive the pump unit 14 therein. As the pump unit is received in the bed 40, the pump unit is placed into fluid communication with the cannula through a port 32 within the cannula receiver 30.

The pump unit 14 may have a pump mechanism configured as described, for example, in the aforementioned U.S. application Ser. No. 12/147,283 filed Jun. 26, 2008 and titled DISPOSABLE INFUSION DEVICE WITH REDUNDANT VALVED SAFETY. To that end, the pump unit may include a piston pump that delivers a fixed volume bolus dose of insulin to the patient with each actuation of the device 10. Further, the pump mechanism includes a pair of actuating buttons 42 and 44. A first one of the buttons, when depressed, establishes a fluid path from the pump to the cannula 34. The second button, when depressed, actuates the pump and causes the pump to deliver the fixed volume bolus dose of insulin to the cannula and thus, to the patient. The pump mechanism is arranged so that the fluid path must first be established by the depression of the first button before the second button may be depressed with the first button to operate the piston pump. After the bolus dose is delivered, the piston pump is recharged with insulin as the actuating buttons return to their original positions.

The pump unit 14 includes a lid 46. When the lid is opened a reservoir receiving compartment 48 is revealed. The reservoir compartment is dimensioned for receiving the reservoir 16 such that, as the reservoir 16 is received in the compartment 48, it is placed into fluid communication with the pump mechanism within the pump unit 14.

The reservoir may be prefilled with medicament, such as insulin. As explained above, in order to maximize the shelf life of a pre-filled drug fluid reservoir, the reservoir materials and construction must minimize the loss of moisture vapor to prevent drug degradation. A standard measure of moisture loss through barrier materials is the moisture vapor transmission rate (MVTR). The MVTR is a measure of the passage of water vapor through a substance, and is typically measured in units of gm/m2/day. For a given material and surface area, increased reservoir thickness results in a linear decrease in MVTR. Therefore, 1 mm thick reservoir material will have half the MVTR of ½ mm thick reservoir material. Since MVTR is also a function of surface area, it is advantageous to use the smallest area of material with higher MVTR, and larger areas of material with lower MVTR.

For the detachable drug reservoir embodiments described herein, an important feature is the ability of the reservoir volume to self-adjust depending on the state of fill. As shall be seen subsequently, this may be accomplished by providing a rigid section and flexible section where the flexible section moves to accommodate the increase and decrease in fluid volume. In order for the flexible section to be flexible when comprised of certain desirable materials such as polychlorotrifluoroethylene (PCTFE), cyclic olefin copolymer (COC), cyclic olefin polymer (COP), polyethylene (PE), polypropylene (PP), and the like, it must be very thin which renders it susceptible to a high MVTR due to its diminished thickness.

To compensate for the diminished thickness and high MVTR needed for flexibility, the flexible section can be reduced in area to only serve that portion of the reservoir needed to be flexible, as for example as shall be seen subsequently, around a rim. By using a thin and flexible section around the rim and joining it to a thicker material with lower MVTR in the center section that does not need flexibility, both needed elements of flexibility and low overall MVTR are maintained.

Figure 3:
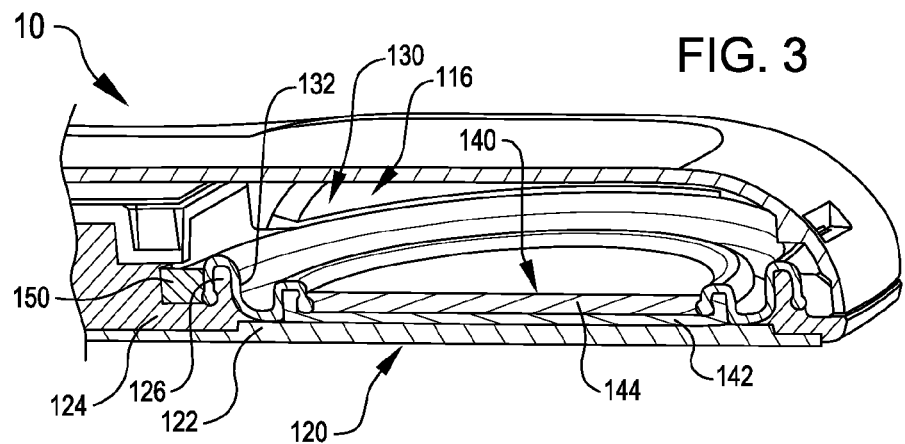
FIG. 3 is a partial perspective view, in section, of the device of FIG. 1 illustrating a first reservoir embodiment of the invention therein in an empty state.
Figure 4:
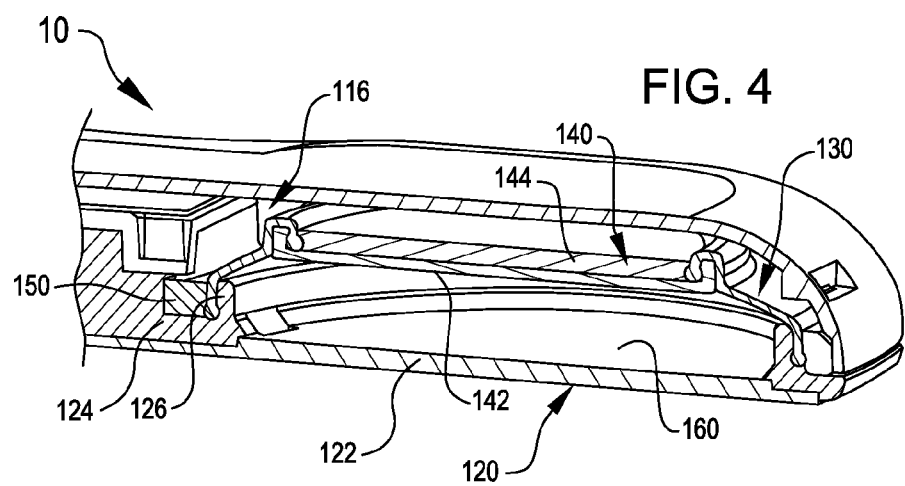
FIG. 4 is a partial perspective view, in section, of the device of FIG. 1 illustrating the first reservoir embodiment of FIG. 3 in a filled state.

FIG. 3 is a partial perspective view, in section, of the device 10 of FIG. 1 illustrating a first reservoir embodiment 116 of the invention therein in an empty state. FIG. 4 illustrates the reservoir 116 in a filled state. As shown in FIG. 3, the reservoir is comprised of a two part rigid base 120, a rolling diaphragm 130, a two part rigid top center section 140 and a clamping ring 150.

The base 120 includes a substantially planar first member 122 and a second member 124 that forms a circular rim 126. The top 140 includes a first substantially planar member 142 and a second substantially planar member 144. The rolling diaphragm 130 has an outer perimeter or edge that is captured and sealed along the perimeter of the base 120 by being pinched and captured between the rim 126 of the base 120 and the clamping ring 150. The rolling diaphragm 130 is also captured and sealed along its inner perimeter or edge to the top center rigid portion 140 by being pinched between the first substantially planar member 142 and the second substantially planar member 144. Although the rigid base 120 is shown in two parts, it may be only a single part. The rolling edge of the diaphragm 130 facilitates the movement of the top rigid center section 140 relative to the rigid base 120.

As may be seen in FIG. 3, the diaphragm has an S-shaped section or profile 132. In the fully filled state as shown in FIG. 4, the rolling diaphragm 130 is fully distended creating a volume 160 containing liquid drug. As shown, the liquid volume contained has a minimal area exposed to the thin, flexible, high MVTR material of the diaphragm 130 and is predominantly contained by the thicker and lower MVTR material of the rigid base 120 and rigid top 140, thus extending the shelf life of the drug substance.

Figure 5:
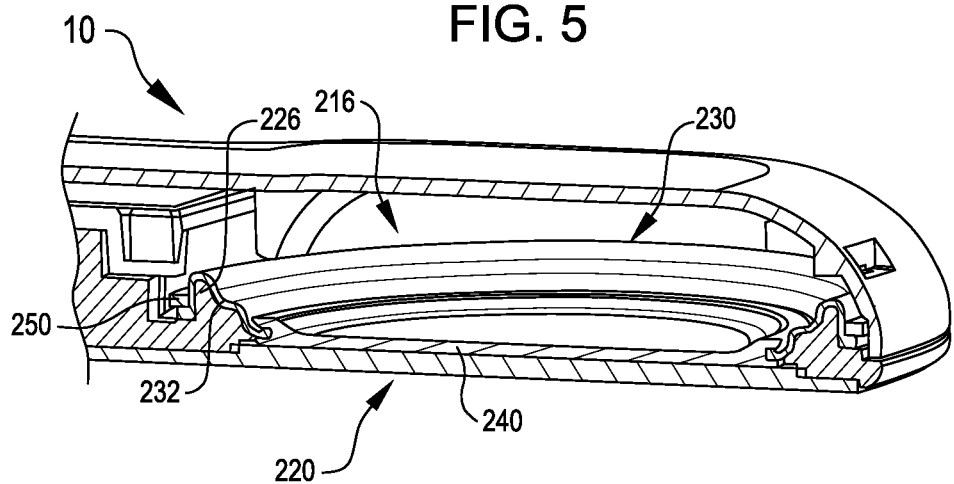
FIG. 5 is a partial perspective view, in section, of the device of FIG. 1 illustrating a second reservoir embodiment of the invention therein in an empty state.
Figure 6:
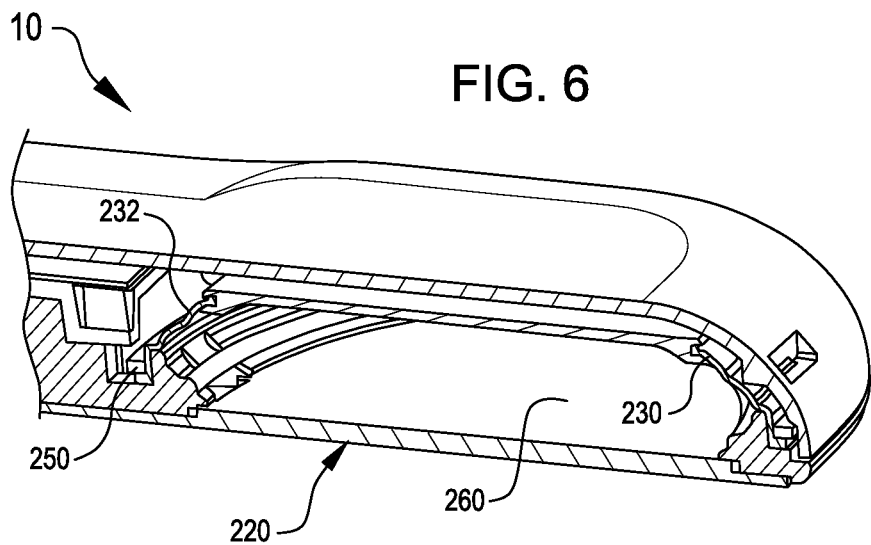
FIG. 6 is a partial perspective view, in section, of the device of FIG. 1 illustrating the second reservoir embodiment of FIG. 5 in a filled state.

FIG. 5 is a partial perspective view, in section, of the device 10 of FIG. 1 illustrating a second reservoir embodiment 216 of the invention therein in an empty state. FIG. 6 shows the reservoir 216 in a filled state. As shown in FIG. 5, the reservoir 216 is comprised of a rigid base 220, a diaphragm 230, a rigid top center section 240 and a clamping ring 250. The base 220 forms a rim 226.

The diaphragm 230 has a molded ripple or accordion-like cross-section 232 to facilitate movement. The rigid top center section 240 is comprised of a single piece, mating around its outer edge with the diaphragm 230. The joint between the diaphragm 230 and the top center section 240 may be made pressure tight by one or a combination of thermal welding, thermal compression, laser welding, ultrasonic welding, adhesive bonding, or the like. The outer edge of the diaphragm 230 is sealed to the base 220 by means of compression ring 250 and rim 226. Alternatively, it may also be sealed to the base by mechanical crimping, thermal, laser, ultrasonic, thermal compression, or adhesive bonding. When filled as seen in FIG. 6, the diaphragm 230 everts creating volume 260 to contain the liquid drug.

Figure 7:
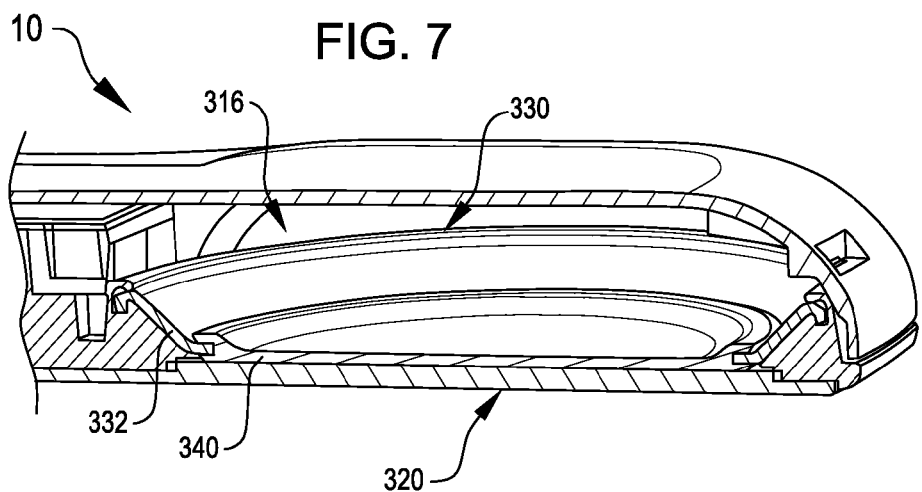
FIG. 7 is a partial perspective view, in section, of the device of FIG. 1 illustrating a third reservoir embodiment of the invention therein in an empty state.
Figure 8:
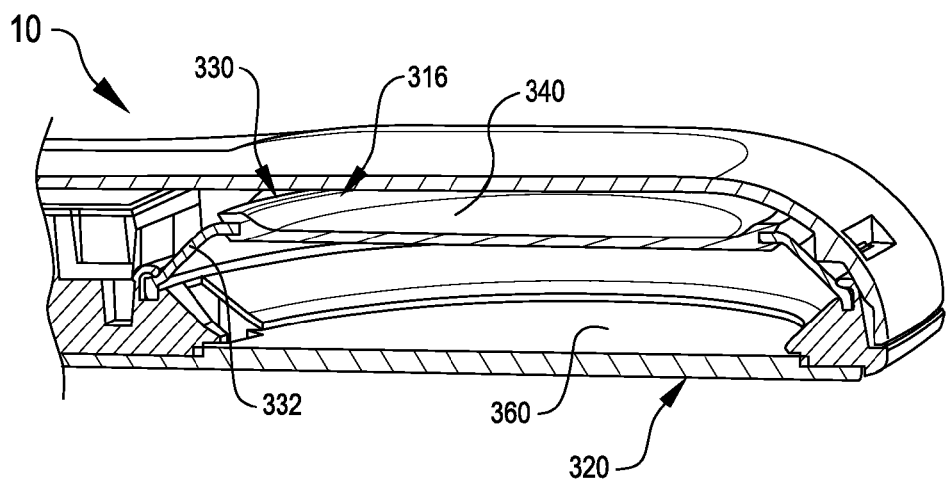
FIG. 8 is a partial perspective view, in section, of the device of FIG. 1 illustrating the third reservoir embodiment of FIG. 7 in a filled state.

FIG. 7 is a partial perspective view, in section, of the device of FIG. 1 illustrating a third reservoir embodiment 316 of the invention therein in an empty state. FIG. 8 illustrates the reservoir 316 in a filled state. As shown in FIG. 7, the reservoir 316 is comprised of a rigid base 320, a diaphragm 330, and a rigid top center section 440. The diaphragm 330 has a smooth configuration or cross-section, better facilitating the manufacture of the diaphragm 330. It is joined to the rigid base 320 and to rigid top 340 at its outer and inner perimeters or edges respectively as previously described by means of thermal compression, compression, crimping, laser welding, ultrasonic welding, thermal welding or adhesive bonding. FIG. 8 shows the filled state creating volume 360 with minimal high MVTR exposed area in diaphragm 330.

While particular embodiments of the present invention have been shown and described, modifications may be made, and it is therefore intended in the appended claims to cover all such changes and modifications which fall within the true spirit and scope of the invention as defined by those claims.

What is claimed is:

1. A reservoir for use in a wearable infusion device, comprising:
   a substantially rigid base, the base having a perimeter;
   a substantially rigid top, the top having a perimeter; and
   a flexible rolling diaphragm between the base and the top, the diaphragm having an outer perimeter sealed along the perimeter of the base and an inner perimeter sealed along the perimeter of the top, the diaphragm being arranged to dispose the top and the base immediately adjacent each other when the reservoir is empty and to dispose the top and the base in spaced apart relation when the reservoir is full.

2. The reservoir as defined in claim 1, wherein the diaphragm has an S-shaped cross-section.

3. The reservoir as defined in claim 1, wherein the diaphragm has an accordion-like cross-section.

4. The reservoir as defined in claim 1, wherein the diaphragm has a smooth cross-section.

5. The reservoir as defined in claim 1, wherein the inner perimeter of the diaphragm is sealed along the perimeter of the top by thermal welding, thermal compression, adhesive bonding, laser welding, ultrasonic welding, mechanical crimping, mechanical clamping or combinations thereof.

6. The reservoir as defined in claim 1, further comprising a clamping ring, wherein the outer perimeter of the diaphragm is in sealed confinement between the clamping ring and the perimeter of the base.

7. The reservoir as defined in claim 1, wherein the top includes a first substantially planar member and a second substantially planar member in surface contact with the first substantially planar member, and wherein the diaphragm inner perimeter is in sealed confinement between the first and second substantially planar members.

8. The reservoir as defined in claim 1, wherein the base includes a first member and a second member, wherein the reservoir further comprises a clamping ring, and wherein the outer perimeter of the diaphragm is in sealed confinement between the clamping ring and the first member of the base.

9. A wearable infusion device, comprising:
   a base arranged to be adhered to the skin of a patient;
   a cannula assembly carried on the base; a pumping unit arranged to be received on the base in fluid communication with the cannula assembly; and a reservoir arranged to be received by the pumping unit, the reservoir including, a substantially rigid base, the base having a perimeter, a substantially rigid top, the top having a perimeter, and a flexible rolling diaphragm between the reservoir base and the top, the diaphragm having an outer perimeter sealed along the perimeter of the reservoir base and an inner perimeter sealed along the perimeter of the top, the diaphragm being arranged to dispose the top and the reservoir base immediately adjacent each other when the reservoir is empty and to dispose the top and the reservoir base in spaced apart relation when the reservoir is full.

10. The device as defined in claim 9, wherein the diaphragm has an S-shaped cross-section.

11. The device as defined in claim 9, wherein the diaphragm has an accordion-like cross-section.

12. The device as defined in claim 9, wherein the diaphragm has a smooth cross-section.

13. The device as defined in claim 9, wherein the inner perimeter of the diaphragm is sealed along the perimeter of the top by one of thermal welding, thermal compression, and adhesive bonding.

14. The device as defined in claim 9, further comprising a clamping ring, wherein the outer perimeter of the diaphragm is in sealed confinement between the clamping ring and the perimeter of the reservoir base.

15. The device as defined in claim 9, wherein the top includes a first substantially planar member and a second substantially planar member in surface contact with the first substantially planar member, and wherein the diaphragm inner perimeter is in sealed confinement between the first and second substantially planar members.

16. The device as defined in claim 9, wherein the reservoir base includes a first member and a second member, wherein the reservoir further comprises a clamping ring, and wherein the outer perimeter of the diaphragm is in sealed confinement between the clamping ring and the first member of the reservoir base.

* * * * *